United States Patent
Bahl et al.

(10) Patent No.: US 9,364,042 B2
(45) Date of Patent: Jun. 14, 2016

(54) FOOTWEAR DISPLAY APPARATUS AND METHOD

(71) Applicant: Reebok International Limited, London (GB)

(72) Inventors: Tyler Bahl, Boston, MA (US); Nathan Martin, Pittsburgh, PA (US); Zach Olshenske, Dravosburgh, PA (US); D. W. Wilson Hamilton, New Alexandria, PA (US)

(73) Assignee: REEBOK INTERNATIONAL LIMITED, London (GB)

( * ) Notice: Subject to any disclaimer, the term of this patent is extended or adjusted under 35 U.S.C. 154(b) by 1 day.

(21) Appl. No.: 14/167,429

(22) Filed: Jan. 29, 2014

(65) Prior Publication Data

US 2014/0214502 A1   Jul. 31, 2014

Related U.S. Application Data

(60) Provisional application No. 61/759,245, filed on Jan. 31, 2013.

(51) Int. Cl.
*G08B 21/00* (2006.01)
*A43B 3/00* (2006.01)
*A43C 19/00* (2006.01)

(52) U.S. Cl.
CPC ............ *A43B 3/0005* (2013.01); *A43B 3/0021* (2013.01); *A43C 19/00* (2013.01)

(58) Field of Classification Search
CPC ..... A43B 3/0005; A43B 3/0021; A43C 19/00
USPC ......................................................... 340/540
See application file for complete search history.

(56) References Cited

U.S. PATENT DOCUMENTS

| | | | | |
|---|---|---|---|---|
| 5,714,706 | A * | 2/1998 | Nakada | A43B 3/0005 36/139 |
| 6,788,200 | B1 * | 9/2004 | Jamel et al. | 340/539.13 |
| 8,739,639 | B2 * | 6/2014 | Owings et al. | 73/862.046 |
| 2006/0097875 | A1 * | 5/2006 | Ott | 340/572.1 |
| 2010/0223815 | A1 * | 9/2010 | McGarity | 36/136 |
| 2012/0239470 | A1 * | 9/2012 | Goldburt | 705/14.4 |
| 2013/0008058 | A1 * | 1/2013 | Jasmine | 36/136 |
| 2013/0185003 | A1 * | 7/2013 | Carbeck et al. | 702/41 |

* cited by examiner

*Primary Examiner* — Kerri McNally

(74) *Attorney, Agent, or Firm* — Sterne, Kessler, Goldstein & Fox P.L.L.C.

(57) ABSTRACT

A device for presenting information about an article of footwear is disclosed, including: a housing for securing to the article of footwear; a position sensor disposed in the housing for determining a position of the device; a memory for storing information related to the article of footwear being in a first position; and a display for presenting the information about the article of footwear being in the first position based on the position of the device determined by the position sensor.

24 Claims, 10 Drawing Sheets

FOOTWEAR DISPLAY APPARATUS AND METHOD

This application claims priority to U.S. Provisional Patent App. No. 61/759,245 titled "Footwear Display Apparatus and Method," filed Jan. 31, 2013, which is incorporated herein by reference in its entirety.

BACKGROUND OF THE INVENTION

1. Field of the Invention

Embodiments of the present invention generally relate to a device for presenting information about an article of manufacture, and more particularly relate to devices and methods for presenting information about an article of footwear to a customer.

2. Background Art

Modern footwear and apparel include unique features, including uppers, soles, colors, materials, and the like, that may be influential in why a consumer chooses to purchase a particular item. In order to maximize sales, manufacturers and retailers must capture the attention of potential customers. One way of capturing their attention is by presenting information about the article's unique features. What is needed, therefore, is an improved device and method for presenting particular information to a consumer of an article of manufacture, such as, footwear.

BRIEF SUMMARY OF THE INVENTION

In one embodiment, a device for presenting information about an article of footwear includes: a housing for securing to the article of footwear; a position sensor disposed in the housing for determining a position of the device; a memory for storing information related to the article of footwear being in a first position; and a display for presenting the information about the article of footwear being in the first position based on the position of the device determined by the position sensor.

In another embodiment, a method for presenting information to a consumer about an article of footwear includes: providing in a retail setting an article of footwear having a display and position sensor secured thereto for determining when the article of footwear is in a first position; determining with the position sensor that the article of footwear is in the first position; and with the display presenting to a consumer information about the article of footwear specific to the first position based on the determination by the position sensor.

BRIEF DESCRIPTION OF THE DRAWINGS/FIGURES

The accompanying drawings, which are incorporated herein and form a part of the specification, illustrate the present invention and together with the description, further serve to explain the principles of the invention and to enable a person skilled in the pertinent art to make and use the invention.

DETAILED DESCRIPTION OF THE INVENTION

The present invention will now be described in detail with reference to embodiments thereof as illustrated in the accompanying drawings, in which like reference numerals are used to indicate identical or functionally similar elements. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The following examples are illustrative, but not limiting, of the present invention. Other suitable modifications and adaptations of the variety of conditions and parameters normally encountered in the field, and which would be apparent to those skilled in the art, are within the spirit and scope of the invention.

Embodiments of the present invention include a display apparatus 10 for presenting information about an article of manufacture to a user 30. In particular, the apparatus 10 may be used in conjunction with an article of footwear 20 to present information to a consumer about the article of footwear based on the current position of the article of footwear. For example, in a retail setting, an article of footwear 20 may be provided for sale and a display apparatus 10 may be used to present information to a potential customer 30 about the article of footwear 20 specific to the current position of the article of footwear 20. In this manner, in some embodiments the display apparatus 10 may uniquely provide information about particular features of an article of footwear 20 for purchase in order to more effectively capture the attention of a potential customer.

In some embodiments, the term "user" as used herein may include a potential consumer of the article of footwear, a retailer who may be displaying the article of footwear 20 with the apparatus 10 for sale, a manufacturer of the article of footwear 20, and/or other suitable individual.

In one embodiment, with reference to FIGS. 1-11, for example, the display apparatus 10 includes a housing 100, at least one position sensor 130 for determining a position of the apparatus 10 (and, correspondingly, the article of footwear 20), a memory 120 for storing information related to the article of footwear 20, and a display 110 for presenting the information about the article of footwear 20 to a user based on the position determination made by the position sensor 130.

Figure 1:
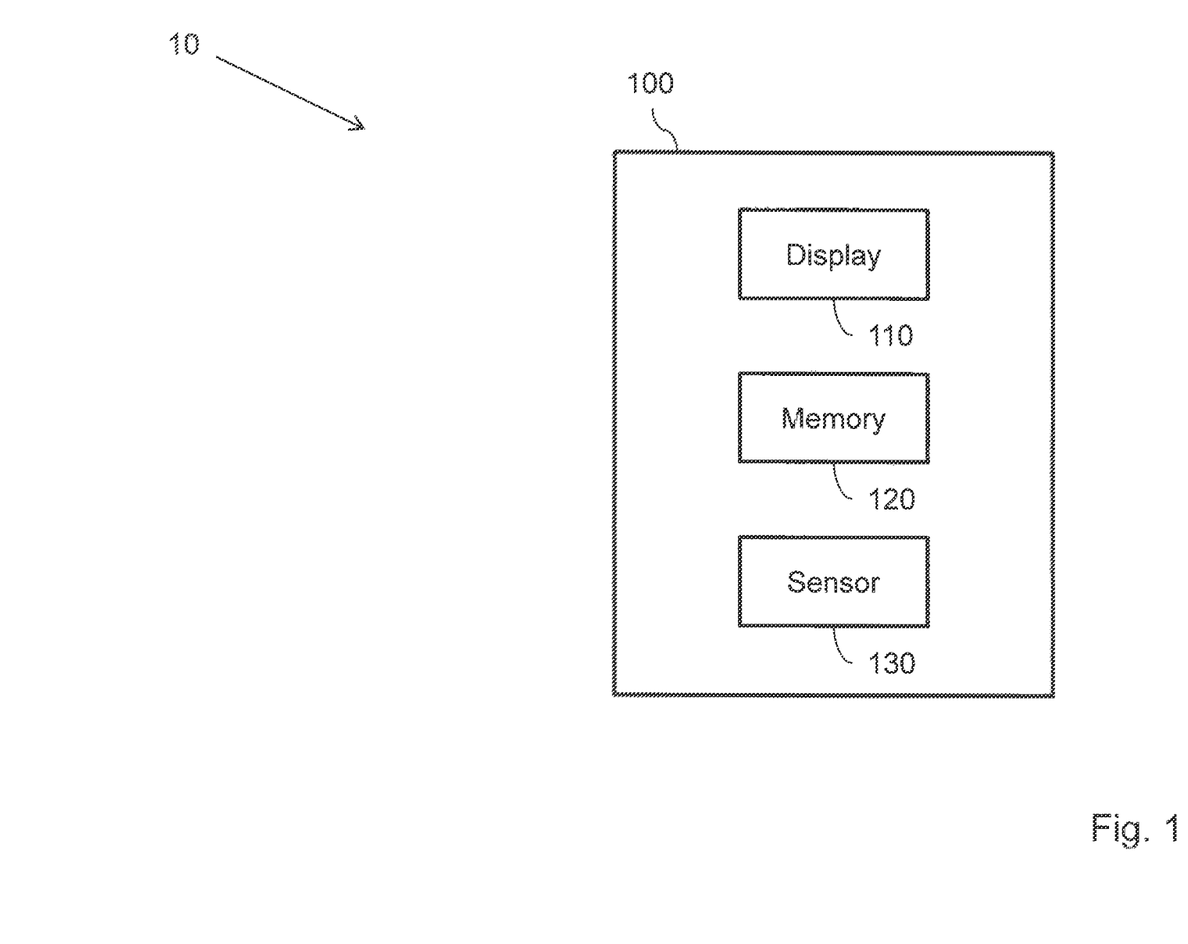
FIG. 1 is a schematic block diagram of a display apparatus according to an embodiment of the present invention.

In one embodiment, the position sensor 130 is disposed in the housing 100. In one embodiment, the position sensor 130 is a multi-axis position sensor adapted to determine an orientation of an object relative to multiple axes. In one embodiment, the position sensor 130 is a gyroscope and may be adapted to determine translational and rotational position information. Other suitable devices for determining the position of the apparatus 10, the housing 100, and/or the article of footwear 20, including, but not limited to, one or more accelerometers, pedometers, GPS receivers, and similar devices, and/or combinations thereof, may be used. In this manner, by determining the position of the display apparatus 10 secured to the article of footwear 20, the position sensor 130 is adapted to determine the position of the article of footwear 20. As such, for example, the position sensor 130 (and corresponding processor) is adapted to determine which portion of the article of footwear 20 is upwardly facing, and, thus, prominently viewable to a user 30. As will be appreciated, the number and placement of position sensors 130 used may vary depending on the size and shape of the article and other needs of the end user. In one embodiment, the position sensor 130 may be an accelerometer and may determine the rate of angular movement in addition to the orientation of the article in one embodiment, the position sensor 130 may he adapted to determine a position of the apparatus 10, the housing 100, and/or the article of footwear 20 out of a set of predetermined positions. For example, the position sensor 130 may include one or more (e.g., an array) of tilt sensors adapted to determine a position of the apparatus 10, the housing 100, and/or the article of footwear 20 (e.g., bottom view) out of a set of predetermined positions (e.g., bottom view, top view, medial side view, lateral side view, front view, and back view).

In some embodiments of the present invention, a position determination may include a determination of the articles absolute position and its orientation within a particular space, such as, for example, a retail setting. In some embodiments, a position determination may include a determination of the article's orientation (e.g., bottom facing up, top facing up, medial side facing up, lateral side facing up, front facing up, and back facing up).

In one embodiment, the position sensor 130 may be disposed remote from the housing 100 of the display apparatus 10. For example, the position sensor 130 may be disposed in a cavity formed in the sole of the article of footwear 20, or otherwise disposed on the article of footwear 20 apart from the display apparatus 10, and may be in wireless or wired communication with the display apparatus 10.

The memory 120 is configured to store information related to the article of footwear 20, and, more particularly, information related to the article of footwear 20 being in a particular position. For example, in one embodiment, the memory 120 may store audio files related to the article of footwear 20 being in a particular position. In one embodiment, as shown for example in FIG. 2, the memory 120 comprises a memory card 122 which may be removably disposed in a slot 124 in the housing 100. The memory card 122 may comprise a non-volatile memory card, such as an SD card by SanDisk, or the like. By providing the memory 120 in a manner such that it is easily removable from the housing 100, the display apparatus 10 in some embodiments may be quickly and easily customizable to the article of footwear 20 being displayed. Other suitable memory devices, including, but not limited to, a USB flash drive, a memory cartridge, a hard drive, a CD-ROM, a removable memory chip (such as an EPROM or PROM), solid state storage, and the like, may be used. As will be appreciated, the memory 120 may include the information in a format that is accessible to and may be processed by one or more processors of the display apparatus 10. In one embodiment, the memory 120 may be remote from the housing 100 of the apparatus 10 and may be accessed over a wireless or wired connection (e.g., a network or the Internet). In this manner, the display apparatus 10 may be adapted to wirelessly receive audio files over a network. in one embodiment, the memory 120 may not be removable from the housing 100.

The display 110 is adapted to present information about the article of footwear 20, for example, to a potential customer in a retail setting. In one embodiment, as shown for example in FIG. 2, the display 110 includes a speaker 112 for audibly presenting information about the article of footwear 20 to the user. In one embodiment, as shown for example in FIG. 15, the display 110 may include a visual display 114 in addition to, or instead of the speaker 112 for presenting visual information to the user. In one embodiment, the display apparatus 10 includes a voice synthesizer, or other suitable module, for converting the readable information stored in the memory 120 to audible information presented to the user. In one embodiment, the user 30 may select a particular voice for presenting audible information. For example, the user 30 may select a voice based on gender, a particular athlete or celebrity voice, or other suitable voice selection options.

The display apparatus 10 may be used in conjunction with any suitable article of footwear. In one embodiment, as shown, for example, in FIGS. 11 and 15, the article of footwear 20 comprises a shoe having an upper 21 attached to a sole 23. In other embodiments, the article of footwear 20 may comprise any type of footwear in which the display apparatus 10 may be desirable for presenting information about the article, including, but not limited to, running shoes, basketball shoes, court shoes, tennis shoes, and sandals.

In one embodiment, the display is adapted to present information specific to the article of footwear 20 being in a particular position, which may he determined by the position sensor 130. This information may include, for example, a description of a feature of the article of footwear 20 that is particularly noticeable from, or relevant to, the particular view the user 30 has of the footwear in its current position.

Figure 12:
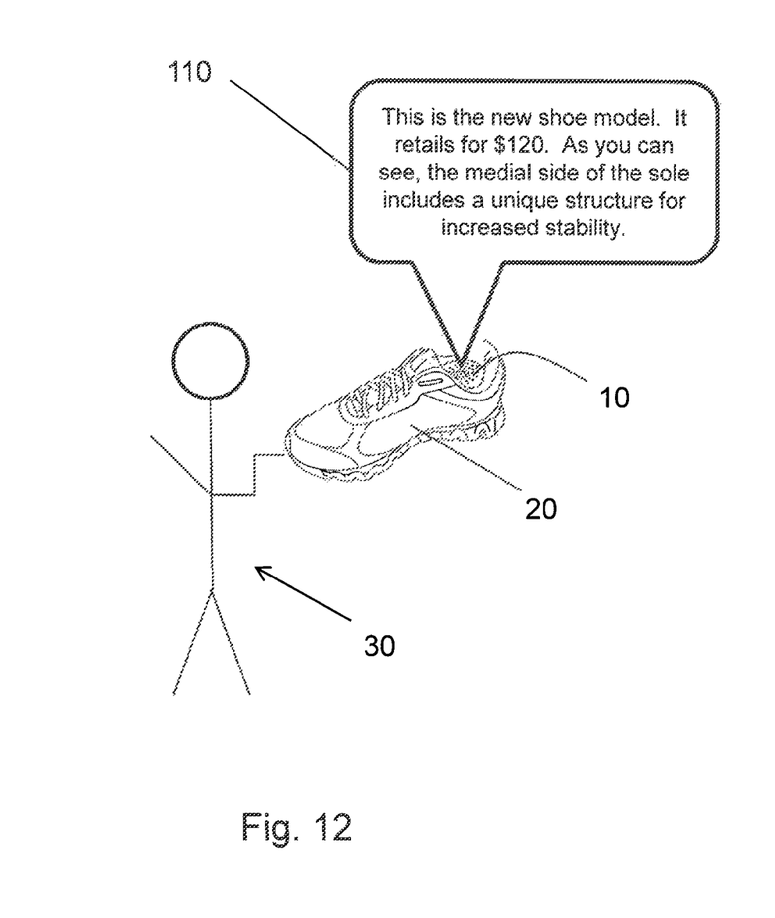
FIG. 12 is a schematic illustration of a display apparatus presenting information specific to an article of footwear being in a top view position according to an embodiment of the present invention.
Figure 13:
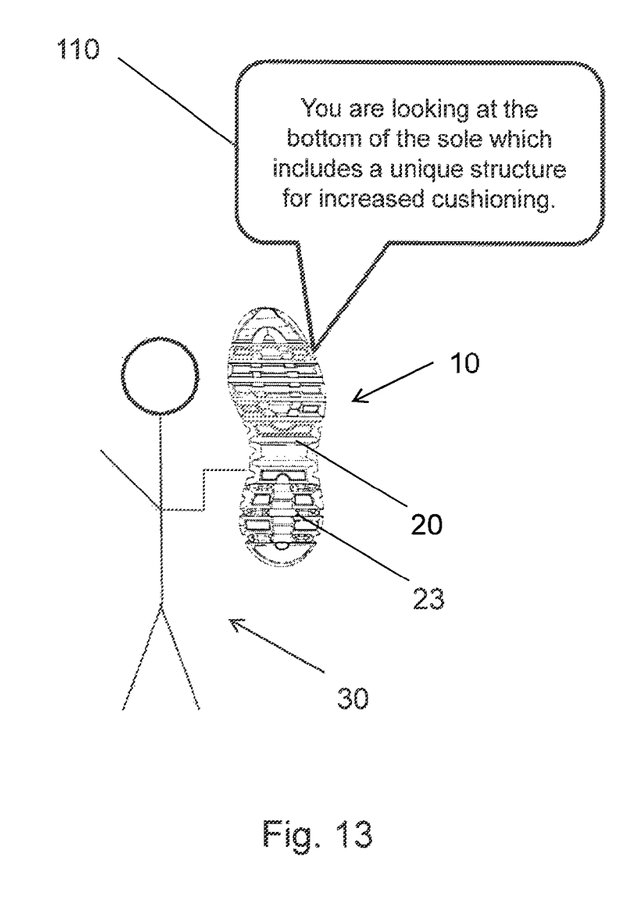
FIG. 13 is a schematic illustration of a display apparatus presenting information specific to an article of footwear being in a bottom view position according to an embodiment of the present invention.

For example, as shown in FIG. 12, the position sensor 130 may determine that the article of footwear 20 is being held by a user 30 in a position whereby the medial side of the footwear is prominent or visible to the user. For example, the article of footwear 20 may be in a position whereby the medial side of the footwear is upwardly facing. Based on this position determination, the apparatus 10 is adapted to access information stored on the memory 120 specific to the article of footwear 20 being in this position (e.g., the medial side of the footwear is prominent or visible to the user) and the display 110 is adapted to present the information to the user 30. For example, the display 110 may audibly speak a message to the user 30 through the speaker 112, such as, "As you can see, the medial side of the sole includes a unique structure for increased stability." Similarly, with reference to, for example, FIG. 13, the position sensor 130 may determine that the article of footwear 20 is being held by a user 30 in a position whereby the bottom of the sole 23 of the footwear 20 is prominent or visible to the user. For example, the article of footwear 20 may be in a position whereby the bottom of the sole 23 of the footwear is upwardly facing. Based on this position determination, the apparatus 10 is adapted to access information stored on the memory 120 specific to the article of footwear 20 being in this position (e.g., the bottom of the footwear is prominent or visible to the user) and the display 110 is adapted to present the information to the user 30. For example, the display 110 may audibly speak a message to the user 30 through the speaker 112, such as, "You are looking at the bottom of the sole which includes a unique structure for increased cushioning."

As will be appreciated, the display apparatus 10 may be adapted to provide information relating to any relevant portion of the article of footwear 20, including but not limited to, the upper, the sole, the outsole, the interior of the footwear, the heel portion, the midfoot portion, and the forefoot portion. Moreover, the display apparatus 10 may be adapted to provide information relevant to any particular viewpoint of any relevant portion of the article of footwear, including, but not limited to, a medial side view, a lateral side view, a bottom view, a top view, a front view, and a back view.

In one embodiment, the display 110 is adapted to provide information about the article of footwear 20 that is not specific to its current position as determined by the position sensor 130. This information may include information about pricing, color, sizing, the brand, sponsors, materials, or any other suitable information for presenting to a potential customer and may be provided in when the article of footwear 200 is in any position, or when it is in each position. For example, as shown in FIG. 12, the display 110 may present a message, such as, "This is the new shoe model. It retails for $120." Such additional information may be stored on the memory 120 and may be provided to the user 30 solely, and/or in addition to the position specific information. In one embodiment, the display 110 may play music related to the article of footwear 20. The music may include music associated with the article of footwear 20 in other marketing initiatives, such as TV commercials.

In one embodiment, the display apparatus 10 includes a housing 100 secured to the article of footwear 20. In one embodiment, the housing 100 may be secured to the article of footwear by way of being disposed within an opening in the article of footwear. For example, with reference to FIG. 11, the housing 100 may be disposed in the opening 22 formed in the upper 21 of the footwear. In one embodiment, the housing 100 may be shaped such that it fits snugly inside the opening 22. For example, the housing 100 may include a curved end portion (e.g., heel portion 102) that is curved to correspond to a heel portion of the article of footwear 20, a tapered middle portion (e.g., midfoot portion 104) that is tapered to correspond to a midfoot portion of the article of footwear 20, and/or a flared or curved end portion (e.g., forefoot portion 106) that is flared and/or curved to correspond to a forefoot portion of the article of footwear 20. In this manner, the housing 100 may have substantially the shape of all or a portion of an interior of the article of footwear 20. Such a housing shape may, in some embodiments, limit movement of the apparatus 10 within the footwear 20 (to reduce likelihood of damage or misalignment, for example) while still allowing the apparatus 10 to be easily removable from the footwear (to provide for re-use or customization, for example), and may keep the apparatus entirely or relatively hidden from the customer. In one embodiment, the housing 100 may be substantially hour-glass in shape.

Figure 15:
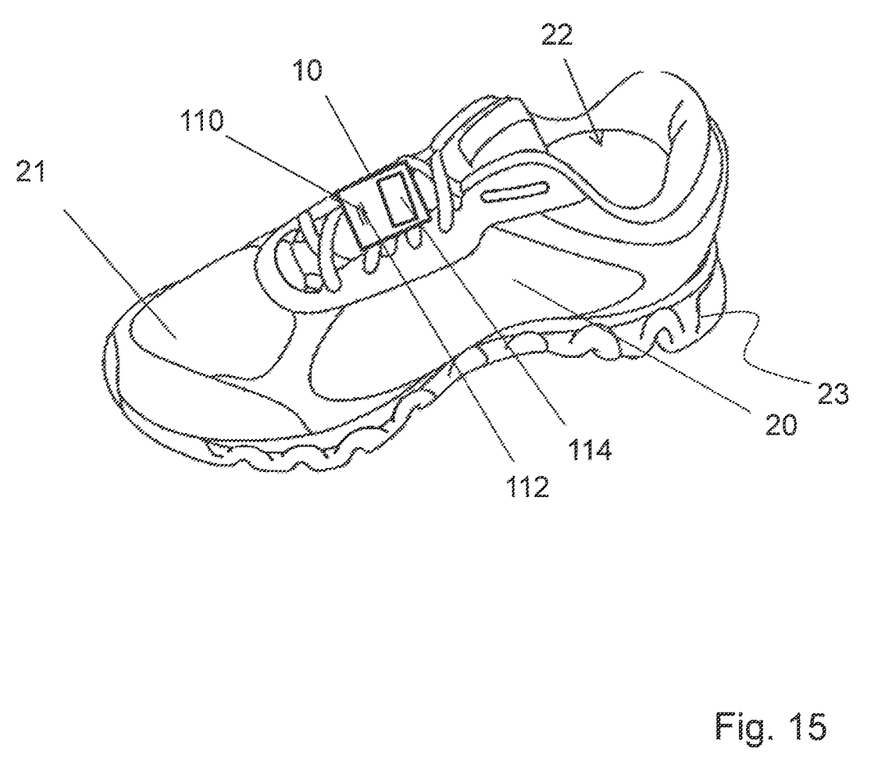
FIG. 15 is perspective view of a display apparatus disposed on an exterior portion of an article of footwear according to an embodiment of the present invention.

In another embodiment, the display apparatus 10 may be disposed on an exterior portion of the article of footwear 20. For example, as shown in FIG. 15, the apparatus 10 may be secured to the laces of the footwear 20. In yet another embodiment, the display apparatus 10 may be disposed in a cavity formed in the sole 23 of the footwear 20. Other suitable means of securing the apparatus 10 to the article of footwear 20 may be used.

Figures 4, 5, 6, 7:
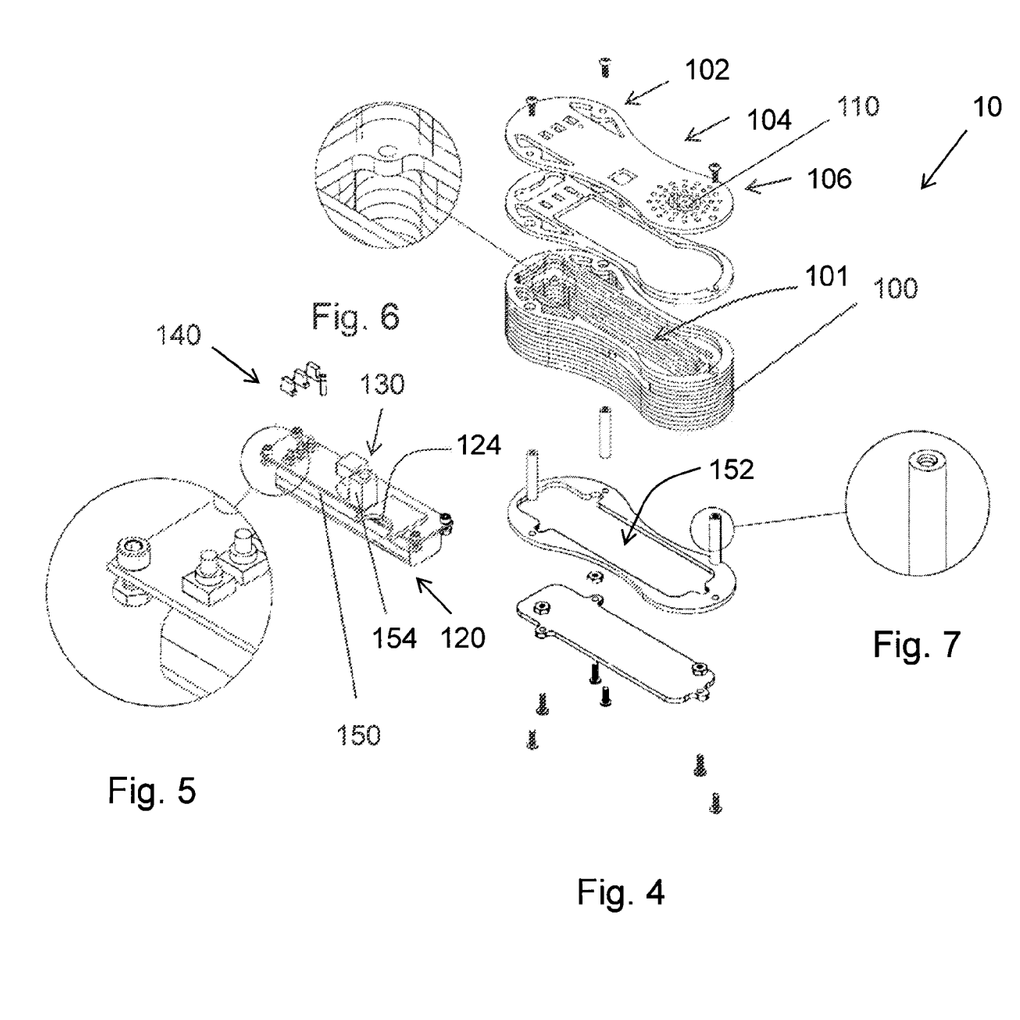
FIG. 4 is an exploded perspective view of a display apparatus according o an embodiment of the present invention.
FIG. 5 is an enlarged partial view of an input control and housing of a display apparatus according to an embodiment of the present invention.
FIG. 6 is an enlarged partial view of a portion of a housing of a display apparatus according to an embodiment of the present invention.
FIG. 7 is an enlarged partial view of a portion of a housing of a display apparatus according to an embodiment of the present invention.
Figure 8:
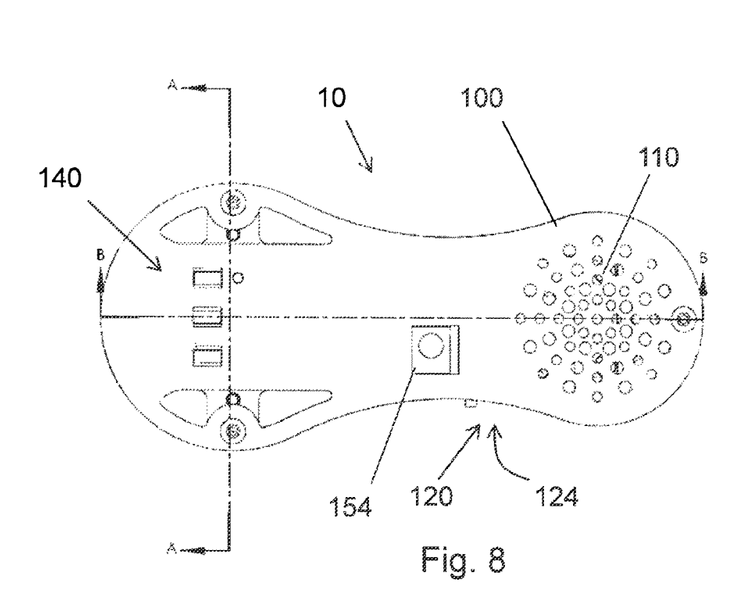
FIG. 8 is a top view of a display apparatus according to an embodiment of the present invention.
Figure 9:
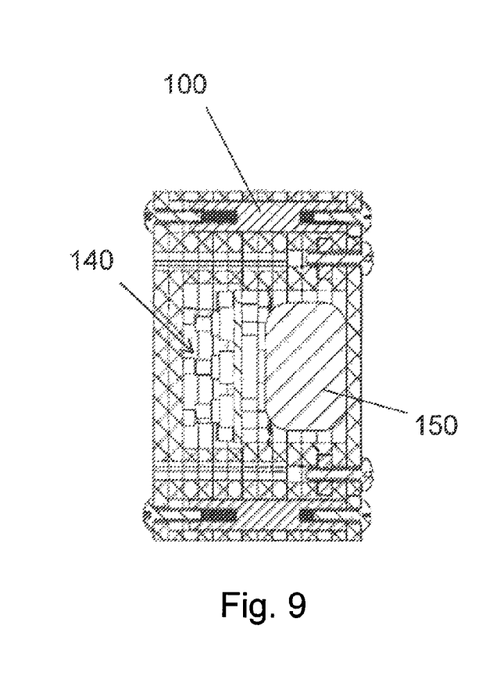
FIG. 9 is a cross-sectional view of the display apparatus of FIG. 8 along the lines A-A.
Figure 10:
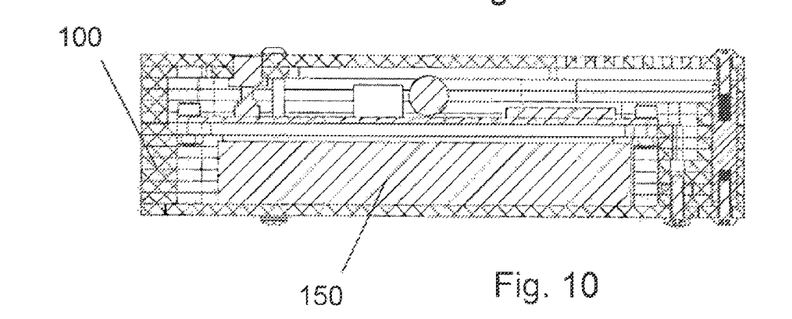
FIG. 10 is a cross-sectional view of the display apparatus of FIG. 8 along the lines B-B.
Figure 11:
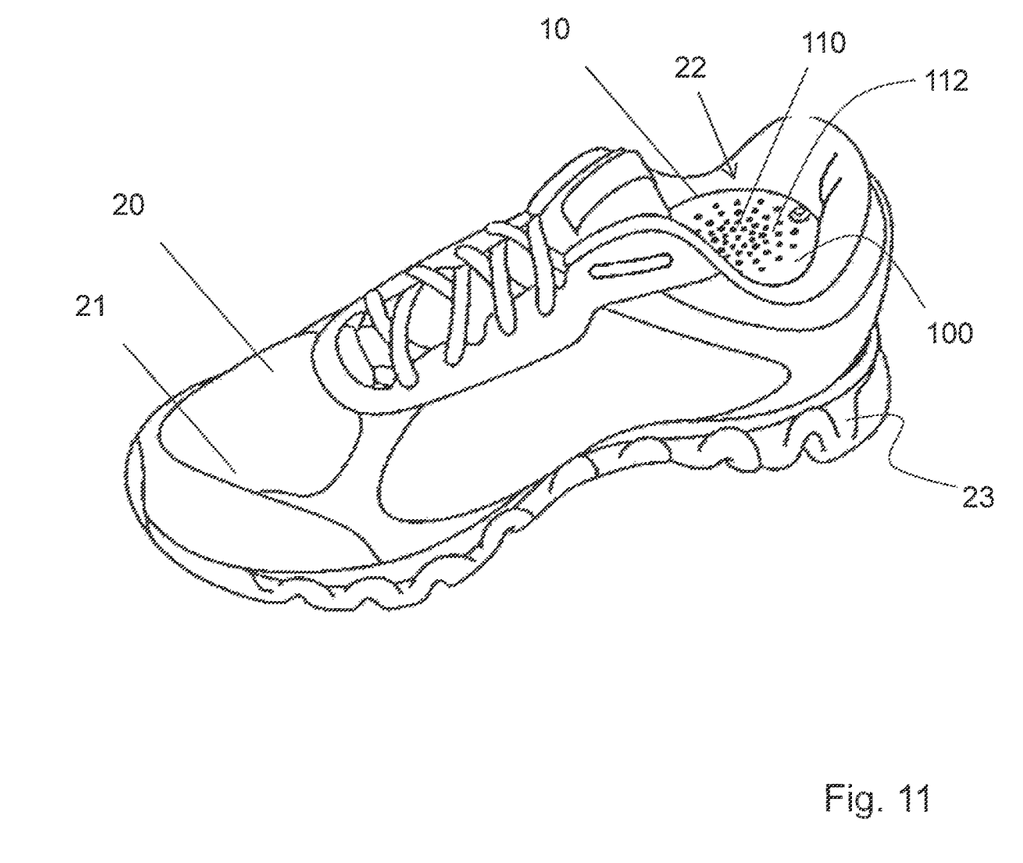
FIG. 11 is a perspective view of a display apparatus secured to an article of footwear according to an embodiment of the present invention.

FIG. 4 is an exploded perspective view of a display apparatus according to an embodiment of the present invention illustrating an exemplary arrangement of components within the housing 100 of the display apparatus 10. In one embodiment, as shown in FIGS. 4 and 6, the housing 100 may include a cavity 101 in which one or more components of the apparatus 10 are disposed.

Figure 2:
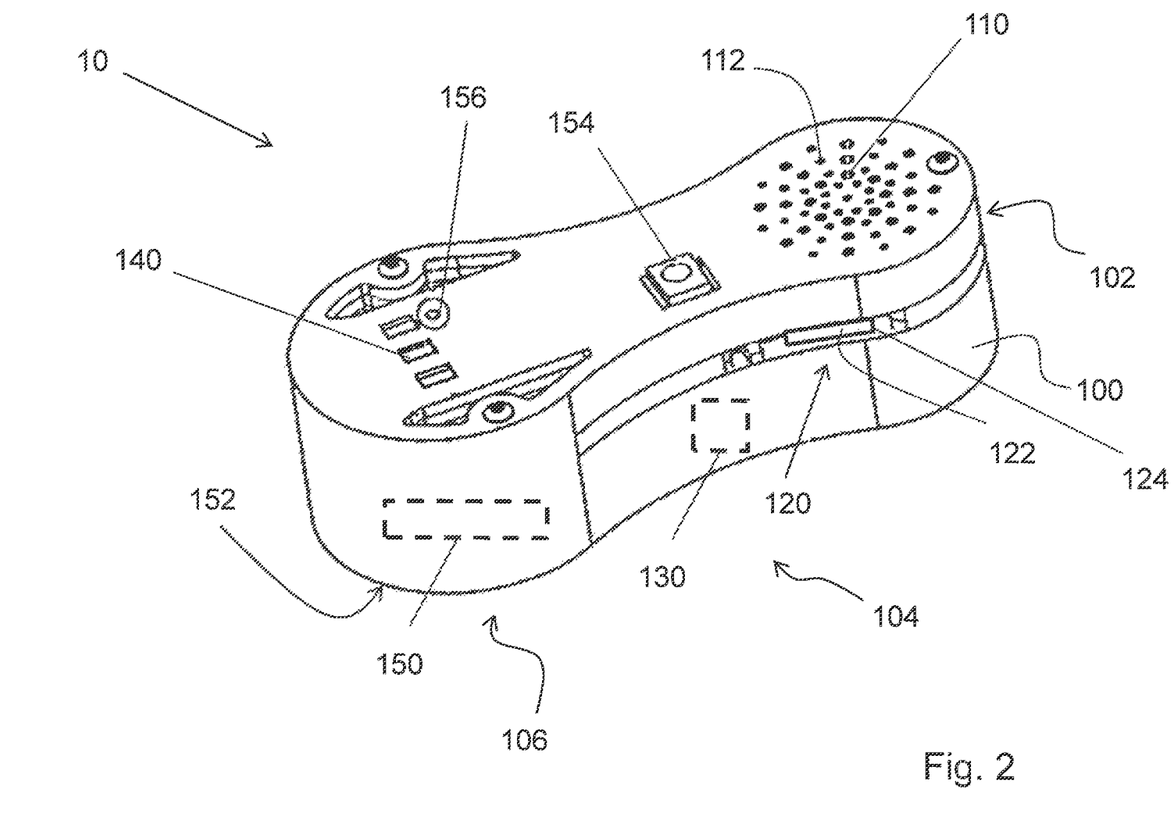
FIG. 2 is a perspective view of a display apparatus according to an embodiment of the present invention.
Figure 3:
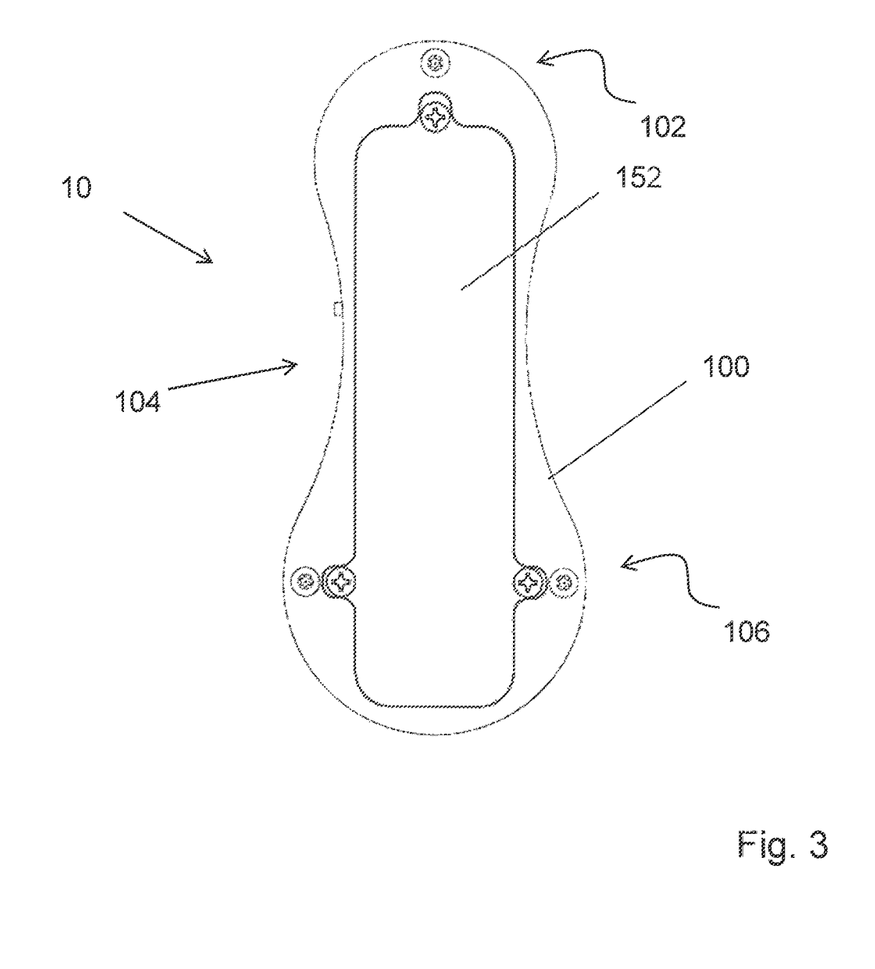
FIG. 3 is a bottom view of a display apparatus according to an embodiment of the present invention.
Figure 14:
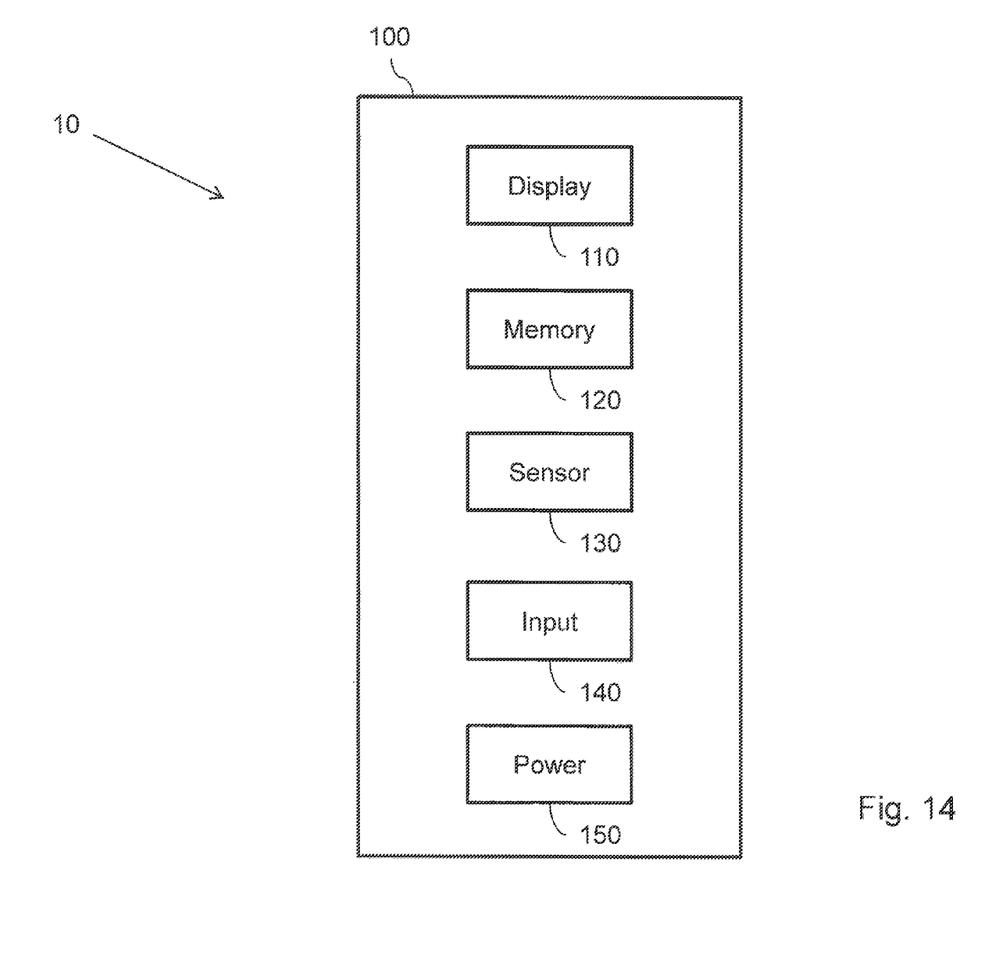
FIG. 14 is a schematic block diagram of a display apparatus according to an embodiment of the present invention.

With reference to FIGS. 2, 4, and 14, in one embodiment the display apparatus 10 may include a power source 150. The power source 150 may be replaceable and/or rechargeable. In one embodiment, the power source 150 may comprise a battery that may be disposed in a compartment 152 formed in the housing 100. In one embodiment, a charging port 154 may be operatively connected to the power source 150 to charge and/or recharge the power source 150. In one embodiment, the charging port 154 is easily accessible from an outer surface of the housing 100, as shown, for example, in FIG. 2. In other embodiments, the display apparatus 10 may include other power sources 150, including, but not limited to, AC/DC, solar, or other suitable means. In one embodiment, the display apparatus 10 may include a status indicator 156 for indicating the status of the power source 150. The status indicator 156 may comprise a light, a speaker, and/cm other suitable display. For example, a status indicator 156 displaying a green light may indicate a good charge for the power source 150; a yellow light may indicate a low charge for the power source 150; and a red light may indicate a very low charge and an indication to replace or recharge the power source 150.

With reference to FIGS. 2 and 14, in some embodiments, the display apparatus 10 may include input controls 140 for receiving input from a user. As shown in FIGS. 2 and 5, in one embodiment input controls 140 may include one or more buttons operable by a user to provide input to the display apparatus 10. In one embodiment, input controls 140 may be used to adjust the volume of the display 110. In one embodiment, input controls 140 may be used to set the language for any audible information presented through the display 110. In one embodiment, input controls 140 may be used to set the desired voice for any audible information presented through the display 110. In one embodiment, input controls 140 may be used to display the power source status on the status indicator 156. In other embodiments, the input controls 140 may be used to provide other desirable functionality to the display apparatus 10.

Figure 16:
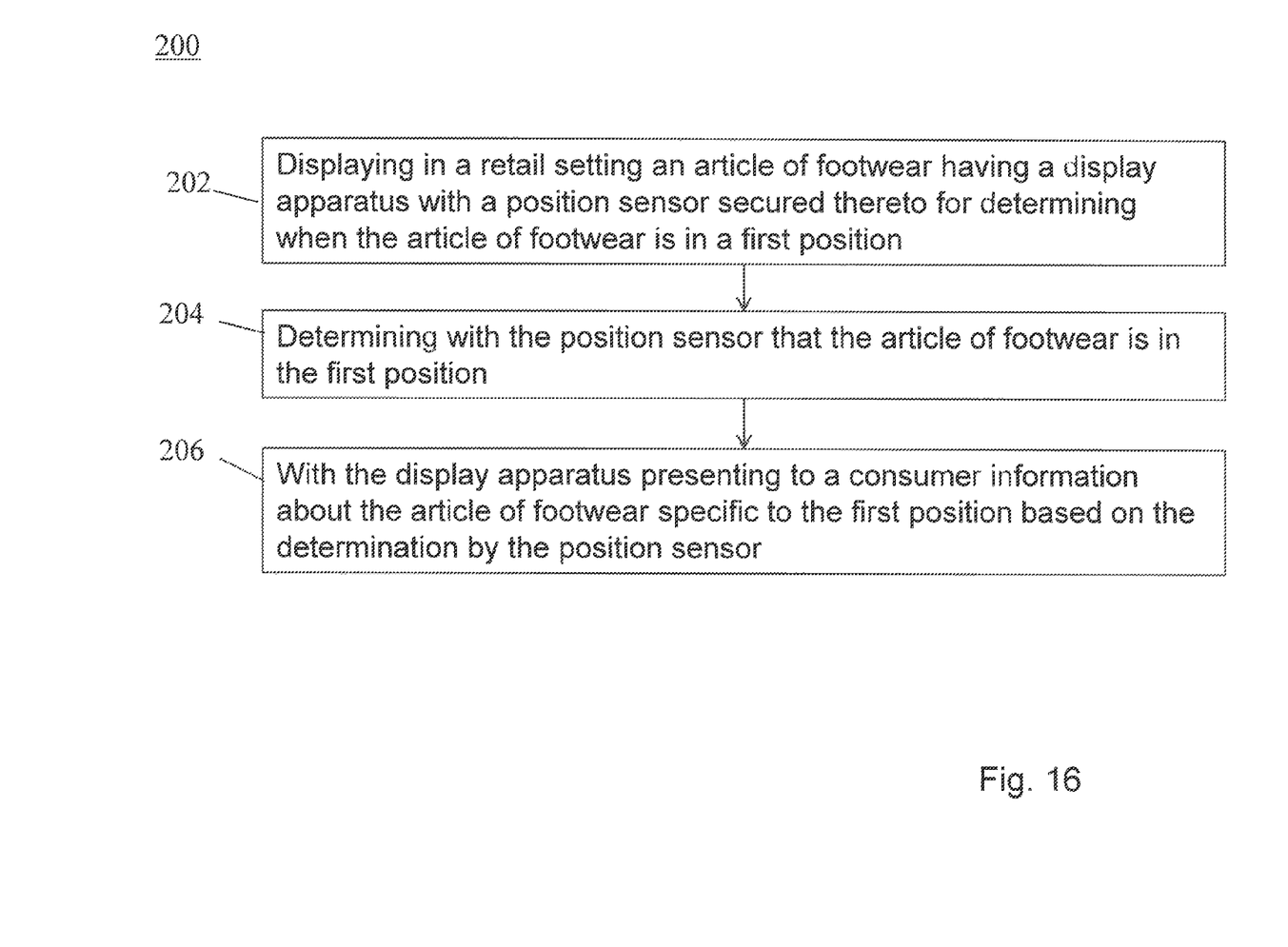
FIG. 16 is a flow diagram of a method of presenting information to a consumer of an article of footwear according to an embodiment of the present invention.

FIG. 16 is a flow chart diagram of an exemplary method 200 for presenting information to a consumer about an article of footwear according to an embodiment of the present invention. Method 200 includes at least steps 202, 204, and 206. For ease of explanation, display apparatus 10 of FIGS. 1-15, as described above, will be used to describe method 200, but are not intended to be limited thereto.

In step 202, an article of footwear 20 is displayed in a retail setting with a display apparatus 10 and a position sensor 130 secured thereto. For example, the display apparatus 10 may be disposed in an opening in the article of footwear 20. In step 204, the display apparatus 10 is configured to determine that the article of footwear 20 is in a first based on position information determined by the position sensor 130. For example, the display apparatus 10 may determine that the article of footwear 20 is in a position, whereby the medial side of the footwear is upwardly facing. In step 206, the display apparatus presents to a consumer 30 information about the article of footwear 20 specific to this medial side position based on the position determination. For example, based on this medial side position determination, the apparatus 10 is adapted to access information stored on the memory 120 specific to the article of footwear 20 being in this position (e.g., the medial side of the footwear is prominent or visible to the user) and the display 110 is adapted to present the information to the user 30. For example, the display 110 may audibly speak a message to the user 30 through the speaker 112, such as, "As you can see, the medial side of the sole includes a unique structure for increased stability."

In some embodiments, the display apparatus 10 may be adapted for use with other articles of manufacture 20 other than an article of footwear. For example, the display apparatus 10 may be used in conjunction with apparel, music instruments, sporting equipment, such as, golf clubs, racquets, hockey sticks, lacrosse sticks, skateboards, bicycles, and other suitable consumer products. In some embodiments, the display apparatus 10 may he used in conjunction with a consumer product having a cavity or opening for receiving the display apparatus 10.

In one embodiment, the display apparatus 10 may be adapted to interact with other external devices to provide additional information to the customer and enhance the overall retail experience. For example, the display apparatus 10 may be adapted to interact with a second display remote from the apparatus 10, such as a large TV screen in the retail setting, to provide additional information. In embodiments in which the display apparatus 10 has wireless capability, the display apparatus 10 may communicate wirelessly with the external device.

As will be appreciated, one or more of the components of the display apparatus 10, including, but not limited to, the display 110, the memory 120, the position sensor 130, the input controls 140, and the power source 150 are operatively connected to one or more processors having computer readable instructions stored thereon to direct the functions of embodiments of the present invention. In some embodiments, the display apparatus 10 may include other components operatively connected to one or more of the components described above, including, but not limited to, an audio amplifier, a video driver, wireless communication chips, and other suitable components as needed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A device for presenting information about an article of footwear, comprising:
   a housing for securing to the article of footwear;
   a position sensor disposed in the housing for determining a position of the device;
   a memory for storing first information related to the article of footwear being in a first position and second information related to the article of footwear being in a second position; and
   a display for presenting the first information about the article of footwear being in the first position when the article of footwear is in the first position and for presenting the second information about the article of footwear being in the second position when the article of footwear is in the second position based on the position of the device determined by the position sensor,
   wherein the first information is different than the second information.

2. The device of claim 1, wherein the display is a speaker.

3. The device of claim 1, wherein the housing is disposed in an interior portion of the article of footwear.

4. The device of claim 1, wherein the housing is substantially the shape of an interior portion of the article of footwear.

5. The device of claim 1, wherein the housing includes a portion shaped to fit the heel portion of an interior of the article of footwear.

6. The device of claim 1, wherein the housing is disposed on an exterior portion of the article of footwear.

7. The device of claim 1, wherein the housing is removably fixed to the article of footwear.

8. The device of claim 1, wherein the position sensor is a gyroscope.

9. The device of claim 1, wherein the position sensor is one or more sensors selected from the group consisting of: a gyroscope, an accelerometer, a pedometer, and a GPS receiver.

10. The device of claim 1, wherein the position sensor is a tri-axial position sensor.

11. The device of claim 1, wherein the memory is removable from the housing.

12. The device of claim 1, wherein the memory comprises a memory card.

13. The device of claim 1, wherein the device is adapted to read an ID tag unique to the article of footwear to identify the article of footwear.

14. The device of claim 1, wherein the position of the device includes an orientation of the housing relative to a reference axis.

15. The device of claim 1, wherein the display includes a visual display.

16. The device of claim 1, wherein the first information about the article of footwear being in the first position includes audible information.

17. The device of claim 1, wherein the first information about the article of footwear being in the first position includes audible and visual information.

18. The device of claim 1, wherein the display is adapted to present other information about the article of footwear.

19. The device of claim 1, wherein the housing comprises a curved end portion.

20. The device of claim 1, wherein the housing comprises a tapered middle portion.

21. The device of claim 1, wherein the housing is configured to secure to the article of footwear by securing to laces of the article of footwear.

22. The device of claim 1, wherein the housing is configured to secure to the article of footwear by being disposed within an opening in the article of footwear.

23. The device of claim 22, wherein the opening is formed in an upper of the article of footwear and the housing fits snugly within the opening.

24. A device for presenting information about an article of footwear, comprising:
   a housing for securing to the article of footwear;
   a position sensor disposed in the housing for determining a position of the device, wherein a portion of the article of footwear is upwardly facing when the device is in the position;
   a memory for storing information related to the upwardly facing portion of the article of footwear; and
   a display for presenting the information about the upwardly facing portion of the article of footwear to a user based on the determination by the position sensor that the device is in the position.

* * * * *